United States Patent [19]

Briggs

[11] Patent Number: 4,917,691
[45] Date of Patent: Apr. 17, 1990

[54] MEDICO-SURGICAL COLLECTION BAG HAVING A RATCHET LOCKING RING

[75] Inventor: Peter J. Briggs, Lancing, England

[73] Assignee: Smiths Industries Public Limited Company, London, England

[21] Appl. No.: 304,071

[22] Filed: Jan. 31, 1989

[30] Foreign Application Priority Data

Feb. 2, 1988 [GB] United Kingdom ............... 8802265

[51] Int. Cl.$^4$ ............................................. H61F 5/44
[52] U.S. Cl. ................................................... 604/339
[58] Field of Search .................. 604/332–349, 604/277

[56] References Cited

U.S. PATENT DOCUMENTS

| | | | |
|---|---|---|---|
| 2,585,716 | 2/1952 | Zaetz | 604/342 |
| 4,386,931 | 6/1983 | Nelson | 604/338 |
| 4,623,338 | 11/1986 | Larson | 604/339 |
| 4,828,553 | 5/1989 | Nielsen | 604/339 |

FOREIGN PATENT DOCUMENTS

| | | |
|---|---|---|
| 0255310 | 2/1988 | European Pat. Off. . |
| 841197 | 6/1952 | Fed. Rep. of Germany ...... 604/337 |
| 2153683 | 8/1985 | United Kingdom . |
| 2193098 | 8/1986 | United Kingdom . |
| 2190841 | 12/1987 | United Kingdom . |

Primary Examiner—Jerome L. Kruter
Attorney, Agent, or Firm—Pollock, Vande Sande and Priddy

[57] ABSTRACT

A two-part ostomy bag assembly comprises a bag and a fitment secured around the stoma. The bag has a coupling in the form of a neck with an annular lip which is insertable in a deformable collar in the fitment. A resilient ring embraces the collar and has projecting tabs by which the ring can be tightened to deform the collar about the neck of the bag coupling. The lip prevents full tightening of the ring before the neck is fully inserted in the collar and the lip engages in an annular recess in the collar. The ring is retained in a tightened state by means of a releaseable ratchet arrangement.

11 Claims, 3 Drawing Sheets

MEDICO-SURGICAL COLLECTION BAG HAVING A RATCHET LOCKING RING

BACKGROUND OF THE INVENTION

This invention relates to medico-surgical collection bag assemblies.

The invention is more particularly concerned with two-part ostomy bag assemblies and the like, having a bag that is removable from a fitment attached to a patient around a stoma or other discharge outlet.

Ostomy bags are used to collect faecal matter discharged from a surgically made stoma in the patient's abdomen. In one form of bag the opening to the bag is provided with an adhesive ring which is used to secure the bag directly to the patient's skin around the stoma, or to a peristomal wafer adhered to the skin. The two-part ostomy bag assembly differs from this in that a fitment is adhered to the patient's skin and the bag is separate from this, being mechanically coupled to the bag in a releasable manner. The bag is removed and disposed of when necessary by uncoupling from the fitment which remains in place to receive a new bag. The fitment can remain in place for several days before it also needs to be removed. Various forms of two-part assemblies have been proposed. These generally include a push-on, snap-fit type of coupling or some form of separate band that embraces the material of the bag around its opening after the bag material has been pushed over the patient's fitment. Both these forms of assembly suffer from various disadvantages since they are either difficult for the patient to use or cause discomfort during coupling or uncoupling. The difficulty of coupling and uncoupling previous assemblies can sometimes disturb the seal of the body-worn fitment with the skin and lead to leakage.

BRIEF SUMMARY OF THE INVENTION

It is an object of the present invention to provide an improved form of two-part bag assembly.

According to one aspect of the present invention there is provided a two-part medico-surgical collection bag assembly in which the first part comprises a collection bag and the second part comprises a patient fitment that is adapted to be secured to the patient around a discharge outlet and to which the bag can be coupled and uncoupled, one of the said parts having a deformable collar and a ring embracing said collar, and the other of said parts having a neck with an external dimension substantially the same as the internal dimension of said collar such that the neck is freely insertable in the collar when the ring is in an open state and such that when the ring is tightened the collar is deformed about the neck of the other part such as firmly to retain the two parts together.

The one part is preferably the patient fitment and the other part is the collection bag. The neck preferably has a radial projection that engages a recess in the collar when the ring is tightened and that may prevent full tightening of the ring before the neck is fully engaged in the collar. The ring may be tightened by reducing its effective circumference. The ring is preferably urged resiliently to an open state and may comprise two substantially rigid arms linked by a resilient web. The ring may be provided with a ratchet arrangement to retain the ring in its tightened state. The ratchet arrangement may comprise a tongue with a tooth on one part of the ring and a notch on another part of the ring, the tooth being engageable in the notch in the tightened state. The tongue may have an inclined tip which can be displaced by the user to disengage the tooth from the notch. The ring may have two tabs projecting from different parts of the ring which can be squeezed together to tighten the ring about the collar. The tongue preferably projects from one of the tabs through an aperture in the other of the tabs. The bag assembly may be an ostomy bag.

A two-part ostomy bag assembly, according to the present invention will now be described, by way of example, with reference to the accompanying drawings.

DETAILED DESCRIPTION

Figure 1:
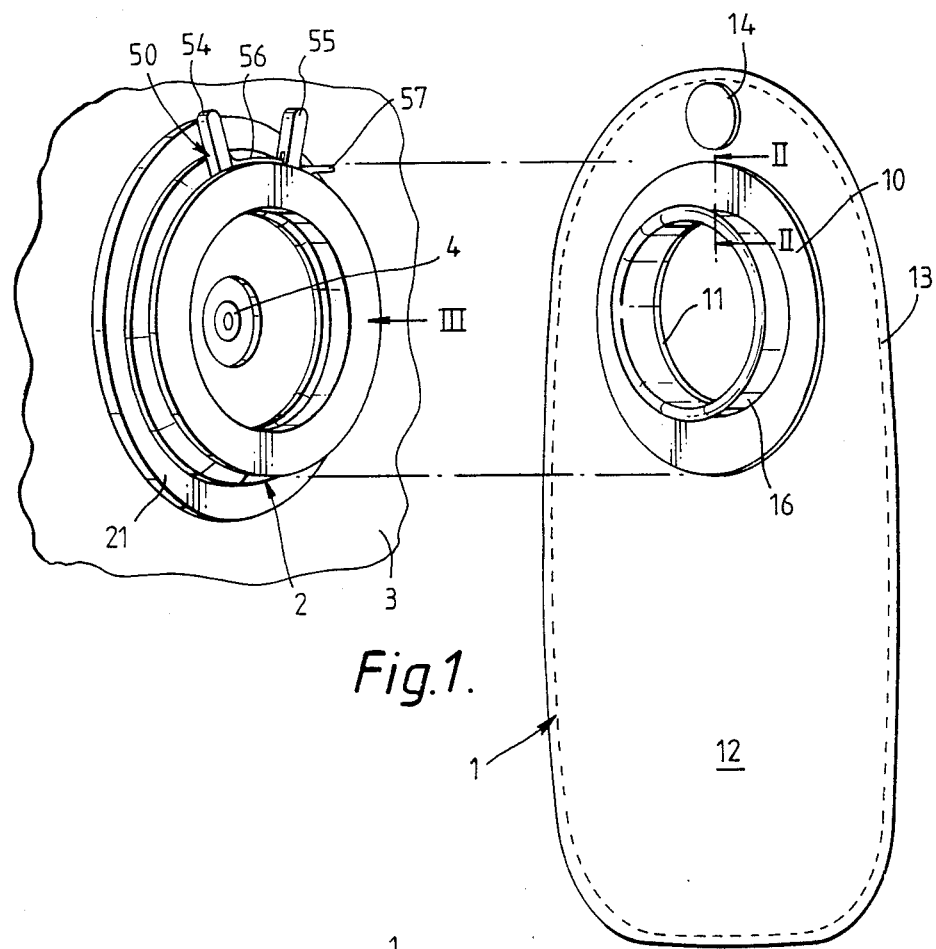
FIG. 1 is perspective view of the assembly.
Figure 2:
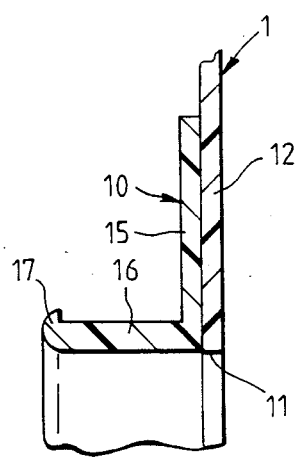
FIG. 2 is a sectional side elevation of a part of the assembly along the line II—II of FIG. 1.

Reference is now made to FIGS. 3 to 6, which show the patient fitment 2 in greater detail. The fitment 2 comprises a one-piece moulding 20 of a deformable plastics material (for example, Kraton) the rear face of which is secured via an adhesive ring 40, or by welding, to an adhesive mounting disc 21 of a hydrophilic polymer in a support matrix of a hydrophobic polymer, such as SEEL-A-PEEL (a Registered Trade Mark of Eschmann Bros. & Walsh Limited). The plastics moulding 20 has an annular, radially-extending flange 23 with a deformable collar 24 of cylindrical shape and circular section that projects axially from the centre of the flange 23. At the outer end of the collar 24, away from the flange 23, an annular wall 25 projects radially outwardly so as to form an annular channel 26 around the moulding 20 between the flange 23 and wall 25. The aperture 27 through the collar 24 is of cylindrical shape and of diameter 73 mm, the aperture being enlarged in diameter to the rear of the collar 24 to form an annular recess 28 and ledge 29. To the rear of the recess, the aperture 27 in the moulding has an inwardly tapering surface 30.

Figure 5:
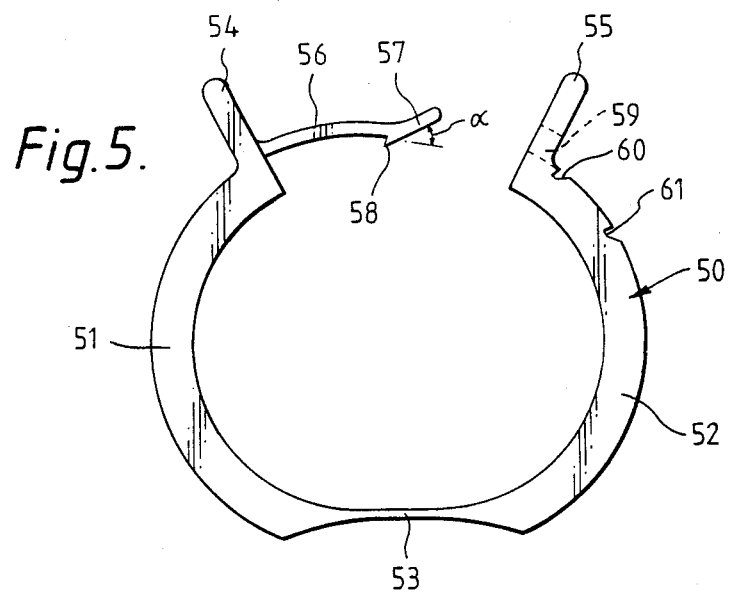
FIG. 5 is a side view of a component of the part shown in FIGS. 3 and 4 in a natural state.
Figure 6:
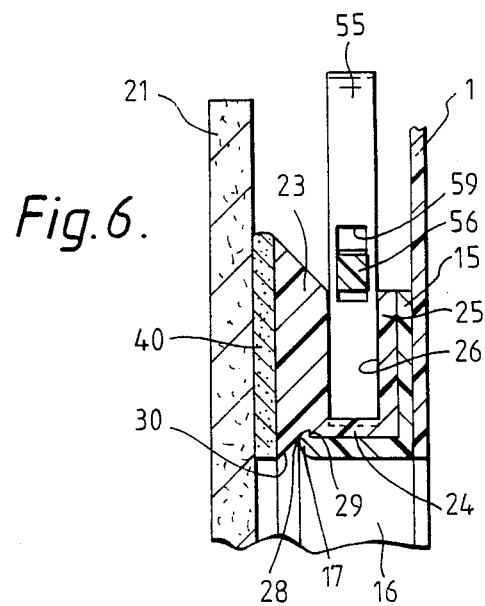
FIG. 6 is a sectional side elevation view showing a part of the bag assembly in an assembled state.

Within the channel 26, around the collar 24, is located an adjustable retaining ring 50 which is shown in detail in FIG. 5. The ring 50 is a one-piece moulding of a thermoplastic material such as ABS and comprises two flat, rigid, semi-circular arms 51 and 52 of rectangular section that are linked together at their lower ends by a thinner, resilient web 53. In its natural state, the upper ends of the arms 51 and 52 lie apart from one another. Both arms 51 and 52 are formed at their upper ends with respective finger tabs 54 and 55 that project radially outwardly by a distance of about 16mm. From one of the tabs 54 there projects a curved tongue 56 of reduced thickness, the arc of which is concentric with that of the arm 51. The tip 57 of the tongue 56 is straight and inclined outwardly at an angle $\alpha$ of 25 degrees to the axis of the tongue, the inner surface of the tongue having an inwardly projecting tooth 58 where the tip inclines outwardly. The other of the tabs 55 is formed with an aperture 59 which aligns with the tongue 56 when the two arms 51 and 52 are pushed together, and through which the tongue can be inserted. Close to the tab 55, on the outer edge of its supporting arm 52, there are formed two notches 60 and 61 which are shaped to receive the tooth 58 on the tongue 56 in a ratchet arrangement.

Figure 3:
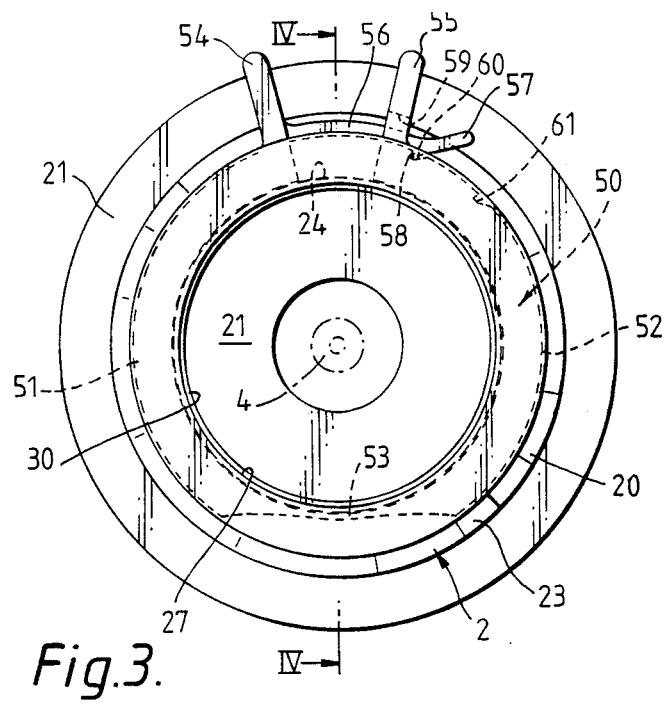
FIG. 3 is an enlarged side view of a different part of the assembly along the arrow III of FIG. 1.
Figure 4:
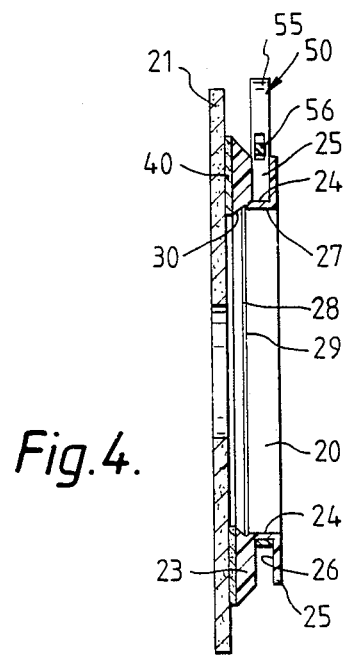
FIG. 4 is a sectional side elevation along the line IV—IV of FIG. 3.

In use, as shown most clearly in FIG. 3, the ring 50 closely embraces the collar 24 of the moulding 20, with the tongue 56 projecting through the aperture 59 and with the tooth 58 engaged with one of the notches 60 or 61. The resilience of the web 53 tends to urge the two arms apart from one another at their upper end thereby retaining the tooth 58 in whichever one of the notches 60 or 61 it is located. The dimensions of retaining ring 50 are such that, with the tooth 58 in the notch 60 closer to the tab 55, the arms 51 and 52 are separated by such a distance that no significant pressure is applied to the collar 24. When, however, the two tabs 54 and 55 are squeezed together, the tongue 56 is pushed further through the aperture 59 and the tooth 58 rides up out of the first notch 60, along the outer edge of the arm 52, until it snaps into the second notch 61. In this position the separation between the two arms 51 and 52 is less, such that the ring 50 is tightened and locked to a smaller effective circumference and a radially inwardly directed force is applied to deform the collar 24 inwardly.

The mounting disc 21 and adhesive ring 40 are preassembled on the moulding 20 so that the user simply has to remove any release sheet (not shown) from the rear face of the mounting disc and press the fitment 2 in position around the stoma.

The retaining ring 50 is put in an open state, if not already in this position, by lifting the tip 57 of the tongue 56 so that the tooth 58 is freed from the second notch 61, thereby allowing the ring to be opened by the resilience of the web 53 until the tooth 58 engages with the first notch 60.

The coupling 10 on the bag 1 is then held up to the fitment 2, the neck 16 being aligned with the aperture 27 in the moulding 20. the external diameter of the neck 16 is such that it can be easily pushed into aperture 27 without exerting any significant force on the skin around the stoma. When the neck 16 has been fully inserted, the flange 15 on the coupling 10 engages the wall 25 on the fitment 2 and the lip 17 aligns with the recess 28 in the collar 24. The retaining ring 50 is then tightened and closed by squeezing together, between finger and thumb the two tabs 54 and 55. This causes the tooth 58 on the tongue 56 to move and lock into the second notch 61 which in turn deforms the collar 24 about the neck 16. In this way, the recess 28 in the collar 24 is pushed onto the lip 17 around the end of the neck 16 so that the lip engages with the ledge 29 and the coupling 10 is firmly secured with the patient fitment 2 in a releasable manner. The bag 1 is readily released from the fitment 2 by lifting the tip 57 of the tongue 56, so that the tooth 58 is freed from the notch 61, thereby allowing the resilience of the ring 50 and collar 24 to open the ring.

The lip 17 on the neck 16 ensures that the coupling 10 is fully engaged with the fitment 2 before it is locked in position, because the extra diameter of the lip 17 prevents the ring 50 being fully closed until the lip is located in the recess 28. Engagement of the lip 17 in the recess 28 mechanically locks the neck 16 into the fitment 2.

The matter discharged from the stoma 4 can now flow into the bag 1 via the fitment 2 and the coupling 10. Because the collar 24 is deformable and is clamped securely about the coupling 10, this ensures that a fluid tight seal is produced with a low risk of leakage.

The assembly of the present invention enables a bag to be coupled to a patient fitment very easily, with one hand holding the bag 1 and the other hand gripping the tabs 54 and 55. This can be readily accomplished, even by patients with impaired vision. The assembly avoids the need to apply any significant force towards the skin surface, thereby avoiding discomfort to patients with tender stoma regions. The construction of the assembly is relatively simple without requiring any metal components and can be light in weight and comfortable to wear.

Various modifications are possible to the assembly. For example, various other forms of ring could be used to deform the collar about the bag coupling. Instead of mounting the collar and ring on the patient fitment, in the manner described, it would be possible to mount them on the bag and to provide a neck on the patient fitment that projected within the collar.

What is claimed is:

1. A two-part medico-surgical collection bag assembly comprising: a first part comprising a collection bag and a second part comprising a patient fitment, said patient fitment including means for securing the fitment around a discharge outlet of the patient, wherein one of said parts includes a deformable collar and a ring, said ring embracing said collar and said ring being displaceable from an open state to a tightened state, and wherein the other of said parts has a neck, said neck having an external dimension substantially the same as the internal dimension of the collar such that the neck is freely insertable in the collar when the ring is in an open state, and the said collar being deformed about the said neck when the ring is tightened such as firmly to retain the two parts together.

2. A collection bag assembly according to claim 1, wherein the said one part is the patient fitment and the said other part is the collection bag.

3. A collection bag assembly according to claim 1, wherein the said collar has a recess therein, and wherein the said neck has a radial projection that engages in said recess when the ring is tightened.

4. A collection bag assembly according to claim 3, wherein the size of the radial projection is such that is prevents full tightening of the ring before the neck is fully engaged in the collar.

5. A collection bag assembly according to claim 1, wherein the ring is tightened by reducing its effective circumference.

6. A collection bag assembly according to any one of the preceding claims, wherein the ring is resilient, and wherein the resilience of the ring urges it to an open state.

7. A collection bag assembly according to claim 6, wherein the ring comprises two substantially rigid arms and a resilient web, said web linking the two arms.

8. A collection bag assembly according to claim 1, wherein the ring includes a ratchet arrangement and said ratchet arrangement retains the ring in its tightened state.

9. A collection bag assembly according to claim 8, wherein the ratchet arrangement comprises a tongue on one part of teh ring and a notch on another part of the ring, and wherein the tongue has a tooth that engages in the notch in the tightened state and a inclined tip which is displaceable by the user to disengage the tooth from the notch.

10. A collection bag assembly according to claim 1, wherein the ring has two tabs and wherein the two tabs project from different parts of the ring such that the ring can be tightened about the collar by squeezing together the tabs.

11. A two-part ostomy bag assembly comprising: a first part comprising an ostomy bag, said ostomy bag having an opening thereto and a substantially rigid neck projecting around the opening, said neck having a radially projecting lip; and a second part comprising a patient fitment, said patient fitment incuding an adhesive layer for securing the fitment around a stoma of the patient, a deformable collar, said collar having an annular recess therein and an interal diameter substantially equal to an external diameter of the neck such that the neck is freely insertable in the collar and the recess receives the lip, a resilient ring, said ring embracing said collar and being displaceable against its resilience from an open state to a tightened state in which said collar is deformed about the said neck and the bag is retained firmly on the patient fitment, and locking means, said locking means being arranged to retain said ring in its tightened state.

* * * * *